(12) United States Patent
Jeffrey

(10) Patent No.: US 11,779,749 B2
(45) Date of Patent: Oct. 10, 2023

(54) FLUID LINE CONNECTOR DEVICE

(71) Applicant: MEDICAL DEVICE CREATIONS LIMITED, Liverpool Merseyside (GB)

(72) Inventor: Peter Jeffrey, Liverpool Merseyside (GB)

(73) Assignee: MEDICAL DEVICE CREATIONS LIMITED, Liverpool (GB)

( * ) Notice: Subject to any disclaimer, the term of this patent is extended or adjusted under 35 U.S.C. 154(b) by 552 days.

(21) Appl. No.: 16/765,519

(22) PCT Filed: Nov. 21, 2018

(86) PCT No.: PCT/GB2018/053367
§ 371 (c)(1),
(2) Date: May 20, 2020

(87) PCT Pub. No.: WO2019/102192
PCT Pub. Date: May 31, 2019

(65) Prior Publication Data
US 2020/0316362 A1     Oct. 8, 2020

(30) Foreign Application Priority Data

Nov. 21, 2017 (GB) ..................... 1719318

(51) Int. Cl.
*A61M 39/20* (2006.01)
*A61M 39/10* (2006.01)

(52) U.S. Cl.
CPC ............ *A61M 39/20* (2013.01); *A61M 39/10* (2013.01); *A61M 2039/1033* (2013.01);
(Continued)

(58) Field of Classification Search
CPC .................. A61M 39/20; A61M 39/10; A61M 2039/1033; A61M 2039/1083;
(Continued)

(56) References Cited

U.S. PATENT DOCUMENTS 3,287,031 A     11/1966  Simmons et al.
5,113,571 A  *  5/1992   Manska ................ A61M 39/10
                                                    285/332
(Continued)

OTHER PUBLICATIONS

International Search Report, pp. 1-2, European Patent Office, dated Feb. 11, 2019.

*Primary Examiner* — David Bochna
(74) *Attorney, Agent, or Firm* — Taft Stettinius & Hollister LLP; Stephen F. Rost

(57) ABSTRACT

A cap for a fluid line connector having a male luer lock fitting, the cap having a first side and a second side opposite the first side, the cap comprising a barrier and a stopper extending axially from the barrier towards the first side of the cap. The barrier defines a keyway centred on a longitudinal axis. The shape of the keyway is configured to permit a correspondingly-shaped female luer lock fitting to pass axially therethrough to engage the male luer lock fitting of the fluid line connector. The stopper is configured to prevent rotation of the correspondingly-shaped female luer lock fitting in the first circumferential direction when a lug of the correspondingly-shaped female luer lock fitting is circumferentially aligned with the stopper.

26 Claims, 2 Drawing Sheets

(52) U.S. Cl.
CPC ............... *A61M 2039/1083* (2013.01); *A61M 2039/1088* (2013.01); *A61M 2039/1094* (2013.01)

(58) Field of Classification Search
CPC .. A61M 2039/1088; A61M 2039/1094; A61M 2039/1027
See application file for complete search history.

(56) References Cited

U.S. PATENT DOCUMENTS

| | | |
|---|---|---|
| 2009/0299339 A1 | 3/2009 | Young |
| 2009/0099552 A1 | 4/2009 | Levy et al. |
| 2009/0187166 A1 | 7/2009 | Young |
| 2015/0032089 A1* | 1/2015 | Way ................... A61M 39/1011 604/535 |
| 2019/0009072 A1* | 1/2019 | Schedler ............... A61M 39/10 |
| 2019/0192843 A1* | 6/2019 | Davis ................... A61M 39/20 |
| 2019/0269898 A1* | 9/2019 | Pütter ................... A61M 39/10 |
| 2020/0078578 A1* | 3/2020 | Uehara ................. A61M 39/10 |
| 2020/0384256 A1* | 12/2020 | Hopkinson ........... A61M 39/10 |

\* cited by examiner

FLUID LINE CONNECTOR DEVICE

This application is a U.S. national stage application under 35 U.S.C. § 371 of PCT International Application Serial No. PCT/GB2018/053367, which has an international filing date of Nov. 21, 2018, designates the United States of America, and claims the benefit of GB Application No. 1719318.6, which was filed on Nov. 21, 2017, the disclosures of which are hereby expressly incorporated by reference in their entirety.

This invention relates to a cap for use in connecting two fluid lines together to form a fluid connection. Particularly, this invention relates to a cap for a fluid line connector having a male luer lock fitting, wherein the cap may prevent a non-corresponding female luer lock fitting from connecting thereto.

BACKGROUND

Luer lock connectors are well known within the medical industry for connecting a fluid container to a fluid feed line e.g. connecting a syringe to an IV line. The connection consists of a male connector and a female connector engaging to provide a fluid tight seal. The male connector typically includes a luer taper configured to be received by the female connector. The male connector often includes a thread which matches lugs of the female connector that are configured to lock the two connectors together. The industry standard for lugs of the female connector is such that there are two lugs positioned opposite one another around the circumference of the female connector. It is known that non-standard luer lock connectors may be used in situations in which it is very important not to connect certain fluid feed lines to certain fluid containers.

EP 2 051 770 B1 describes a connector system including a male connector, a female connector and a barrier configured to allow a correspondingly-shaped female connector to pass therethrough and engage a luer taper and a thread of the male connector. The female connector includes lugs spaced circumferentially around the female connector in a configuration different to the industry standard described above. The barrier of the male connector has a slot shaped to match the circumferential spacing of the lugs of the female connector. It may be time consuming for a user to align the non-standard female connector with the slot of the male connector to form a fluid connection, especially in suboptimal working environments (e.g. low light). Indeed, there is a risk that the user may perpetually rotate the non-standard female connector relative to the male connector whilst attempting to form the fluid connection. Due to the often time-critical nature of using such luer lock connectors, it is desirable to have a system whereby the time taken to connect a male connector to a female connector is minimal.

It is an object of certain embodiments of the present invention to address the above-described disadvantages associated with the prior art.

BRIEF SUMMARY OF THE DISCLOSURE

In accordance with a first aspect of the present invention there is provided a cap for a fluid line connector having a male luer lock fitting, the cap having a first side and a second side opposite the first side, the cap comprising:

a barrier defining a keyway, wherein the keyway is centred on a longitudinal axis; and a guide portion that is radially outward of the barrier, wherein the shape of the keyway is configured to permit a correspondingly-shaped female luer lock fitting to pass axially therethrough to engage the male luer lock fitting of the fluid line connector, and wherein the guide portion has a sloped surface sloped radially outwardly towards the first side of the cap.

In certain embodiments, the sloped surface of the guide portion may extend around the circumference of the barrier.

In certain embodiments, the cap may include a stopper extending axially from the barrier towards the first side of the cap. The stopper is configured to prevent rotation of the correspondingly-shaped female luer lock fitting in a first circumferential direction when a lug of the correspondingly-shaped female luer lock fitting is circumferentially aligned with the stopper. The stopper may include a sloped surface sloped towards the barrier in the first circumferential direction. The sloped surface may be configured to guide the lug of the correspondingly-shaped female luer lock fitting when the female luer lock fitting is rotated in a direction opposite the first circumferential direction.

In accordance with a second aspect of the present invention there is provided a cap for a fluid line connector having a male luer lock fitting, the cap having a first side and a second side opposite the first side, the cap comprising:

a barrier defining a keyway, wherein the keyway is centred on a longitudinal axis; and a stopper extending axially from the barrier towards the first side of the cap, wherein the shape of the keyway is configured to permit a correspondingly-shaped female luer lock fitting to pass therethrough to engage the male luer lock fitting of the fluid line connector, and wherein the stopper is configured to prevent rotation of the correspondingly-shaped female luer lock fitting in a first circumferential direction when a lug of the correspondingly-shaped female luer lock fitting is circumferentially aligned with the stopper.

In certain embodiments, the barrier may comprise two or more circumferentially-spaced barrier portions to define the keyway. Each circumferential spacing may define a slot configured to receive a correspondingly-shaped lug of the correspondingly-shaped female luer lock fitting to permit the correspondingly-shaped female luer lock fitting to pass therethrough. Each barrier portion may have a first sidewall configured to prevent rotation of the correspondingly-shaped female luer lock fitting in the first circumferential direction when a lug of the correspondingly-shaped female luer lock fitting is circumferentially aligned with the first sidewall. Each barrier portion may have a second sidewall configured to prevent rotation of the correspondingly-shaped female luer lock fitting in a direction opposite the first circumferential direction when a lug of the correspondingly-shaped female luer lock fitting is circumferentially aligned with the second sidewall.

In certain embodiments, a first barrier portion of the barrier may comprise a top surface facing towards the first side of the cap. The top surface may have a sloped portion sloped towards the second side of the cap in the first circumferential direction. The sloped portion may be configured to guide the lug of the female luer lock fitting when the female luer lock fitting is rotated in a direction opposite the first circumferential direction. The sloped portion may be adjacent to the second sidewall of the first barrier portion. The top surface may have a flat portion normal to the longitudinal axis of the cap. The flat portion may be adjacent to the first sidewall of the first barrier portion.

In certain embodiments, the stopper may extend axially from a second barrier portion of the barrier. The second barrier portion may be spaced from the first barrier portion in the first circumferential direction to define a slot therebetween so that the stopper is circumferentially opposite to the sloped portion of the first barrier portion.

In certain embodiments, the stopper may have a stopper wall that is coplanar with the first sidewall of the second barrier portion.

In certain embodiments, the stopper may have a sloped surface sloped towards the barrier in the first circumferential direction. The sloped surface may be configured to guide the lug of the correspondingly-shaped female luer lock fitting when the female luer lock fitting is rotated in a direction opposite to the first circumferential direction.

In certain embodiments, the cap may comprise a guide portion that is radially outward of the barrier. The guide portion may have a sloped surface sloped radially outwardly towards the first side of the cap. The sloped surface may extend around the circumference of the barrier.

In certain embodiments, the cap may comprise a part identifier configured to aid a user in distinguishing one keyway shape from another. The part identifier may comprise a tactile indicator.

In certain embodiments, the cap may be a monolithic component.

In certain embodiments, the cap may be configured to couple to a fluid line connector having a male luer lock fitting so that, when coupled, the correspondingly-shaped female luer lock fitting may pass through the cap and threadably connect with the male luer lock fitting.

According to a third aspect of the present invention there is provided a fluid line connector, comprising:

a male luer lock fitting; and a cap according to the first aspect of the invention or the second aspect of the invention;

wherein the fluid line connected is configured so that a correspondingly-shaped female luer lock fitting may pass through the cap and threadably connect with the male luer lock fitting.

In certain embodiments, the male luer lock fitting and the cap may be formed monolithically.

According to a fourth aspect of the present invention there is provided an assembly, comprising:

a fluid line connector according to the third aspect of the invention; and a female luer lock fitting connectable to the fluid line connector, the female luer lock fitting comprising one or more lugs configured to be received by a thread of the male luer lock fitting of the fluid line connector;

wherein the female luer lock fitting has a radial shape corresponding to the keyway of the cap of the fluid line connector so that the female luer lock fitting may connect with the fluid line connector such that a fluid may flow between the female luer lock fitting and the male luer lock fitting of the fluid line connector.

In certain embodiments, the female luer lock fitting may comprise a part identifier configured to aid a user in connecting the female luer lock fitting to a correspondingly-shaped keyway of the cap. The part identifier may comprise a tactile indicator.

BRIEF DESCRIPTION OF THE DRAWINGS

Embodiments of the invention are further described hereinafter with reference to the accompanying drawings, in which.

DETAILED DESCRIPTION

Figure 1:
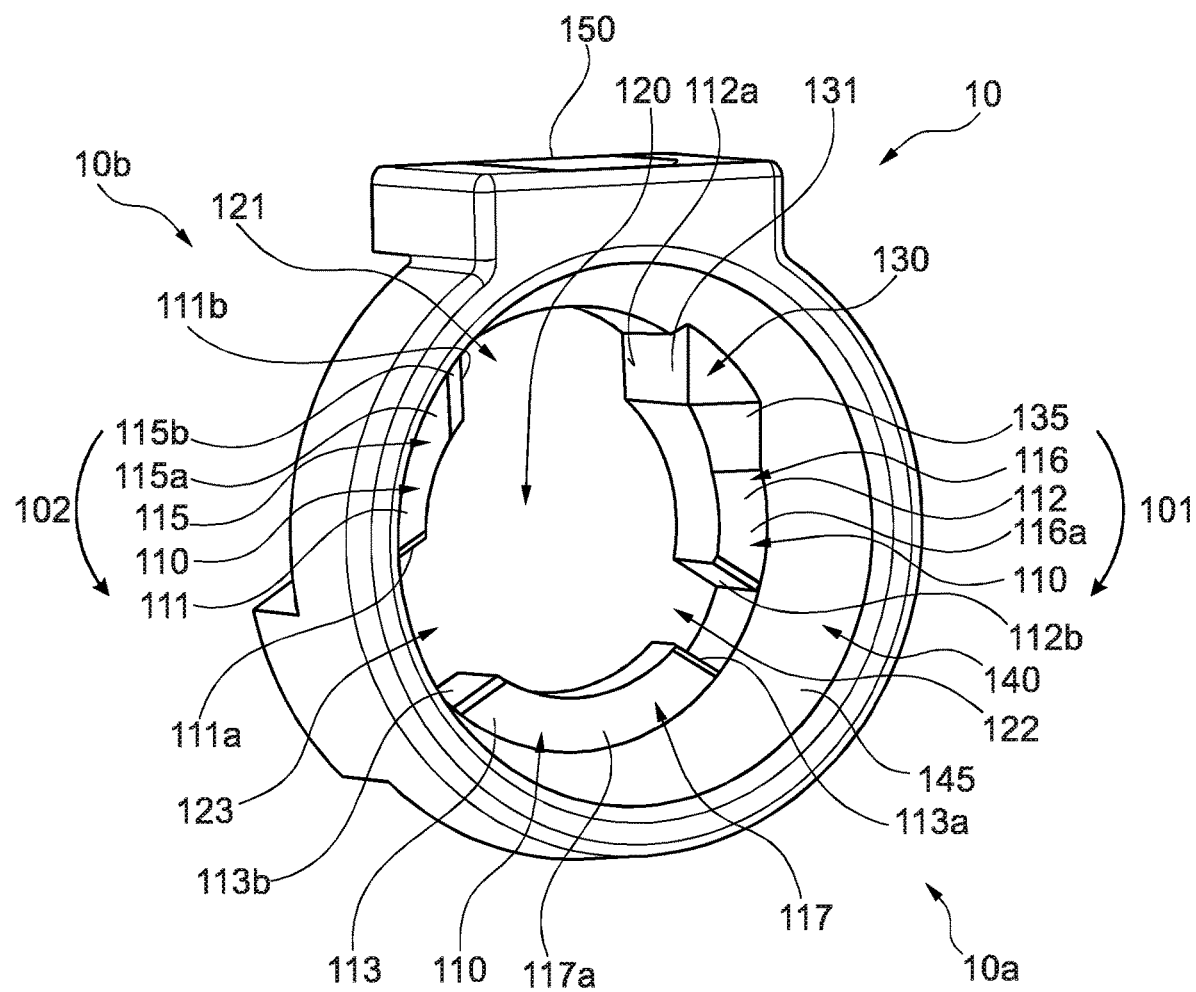
FIG. 1 is a schematic view showing a cap according to an embodiment of the present invention.
Figure 2:
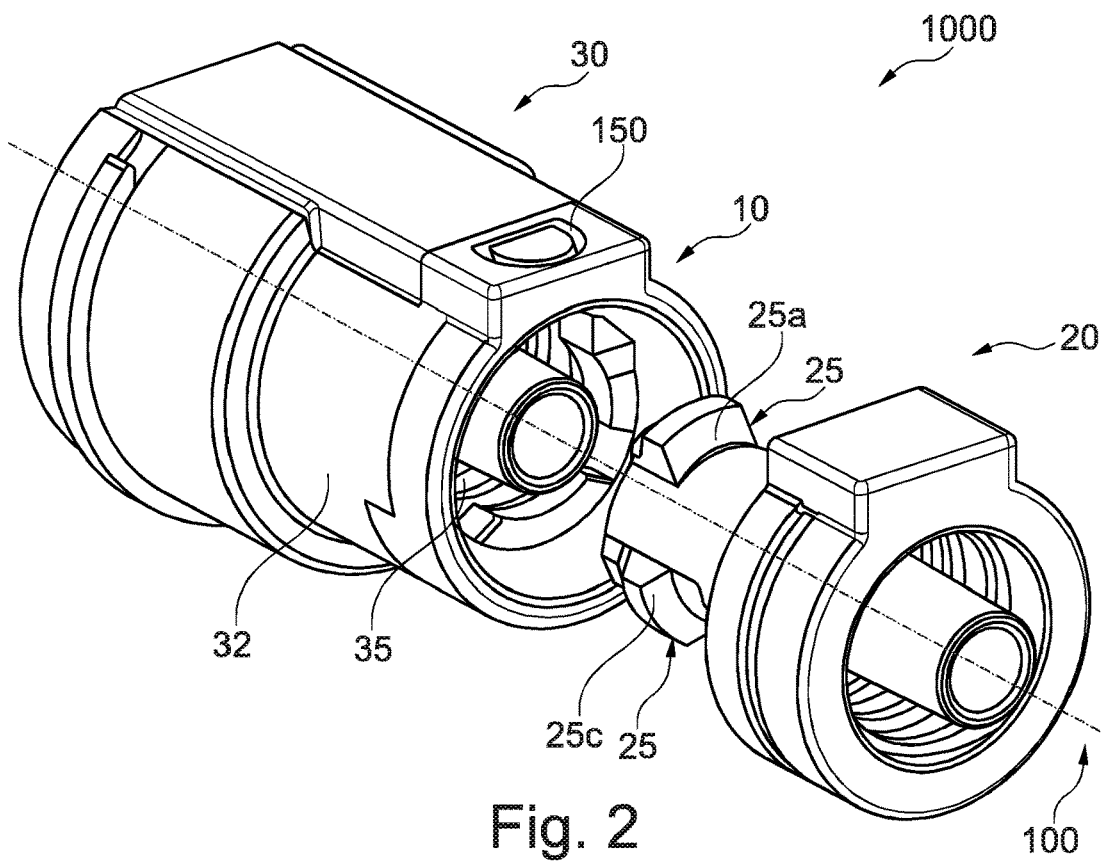
FIG. 2 is a schematic view of an assembly according to an embodiment of the present invention.
Figure 3:
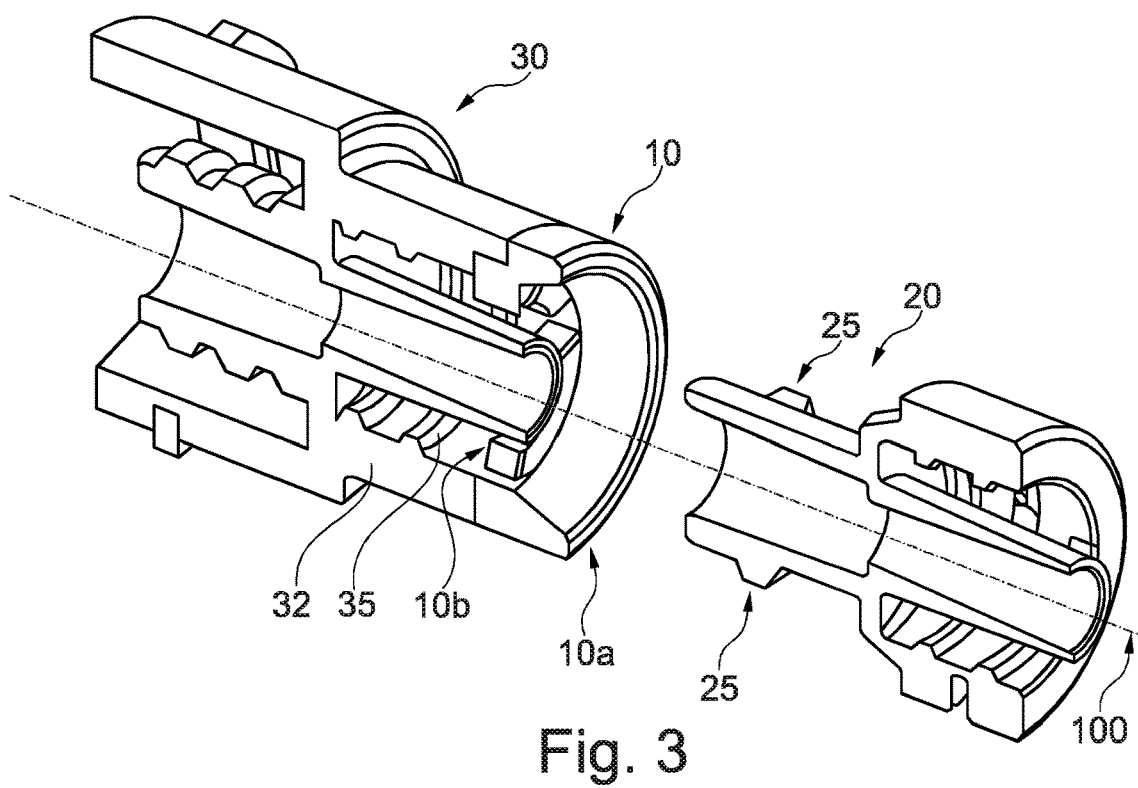
FIG. 3 is a sectional view corresponding to FIG. 2.

A cap 10 in accordance with an embodiment of the present invention is shown in FIG. 1. The cap 10 includes a barrier 110 defining a keyway 120 centred on a longitudinal axis 100 (the longitudinal axis 100 is shown in FIGS. 2 and 3). Throughout this specification, the term "axially" refers to a direction parallel with the longitudinal axis 100, the term "radially" refers to a direction perpendicular to the longitudinal axis 100, and the term "circumferentially" refers to a direction about the longitudinal axis 100.

FIG. 2 shows an assembly 1000 in accordance with an embodiment of the present invention. The assembly 1000 includes a first fluid line connector 30 having a male luer lock fitting 32 and a thread 35, and the cap 10 coupled to the fluid line connector 30. The assembly may include a correspondingly-shaped female luer lock fitting 20 having lugs 25. The keyway 120 of the cap 10 is configured to receive the correspondingly-shaped female luer lock fitting 20 so that the correspondingly-shaped female luer lock fitting 20 may pass axially through the cap 10 to engage a fluid line connector 30. Conversely, a non-correspondingly-shaped female luer lock fitting (not shown) will not be capable of passing through the keyway 120, thus reducing the possibility of inadvertently connecting the fluid line connector 30 to an incorrect fluid feed or outlet.

FIG. 3 shows a sectional view of the assembly of FIG. 2. As shown in FIG. 3, a first side 10a of the cap 10 would generally face the female luer lock fitting 20 prior to the female luer lock fitting 20 passing through the keyway 120 to engage the male luer lock fitting 32 of the fluid line connector 30. A second side 10b of the cap 10 is opposite to the first side 10a of the cap 10 and would generally face the male luer lock fitting 32. As such, the lugs 25 of the female luer lock fitting 20 may pass from the first side 10a of the cap 10 through the keyway 120 to the second side 10b of the cap 10 to engage the thread 35 of the male luer lock fitting 32. A first circumferential direction 101 (identified in FIG. 1) is the direction in which the lugs 25 of the female luer lock fitting 20 must rotate to engage the thread 35 of the male luer lock fitting 32. A second circumferential direction 102 (also identified in FIG. 1) is opposite to the first circumferential direction 101. Typically, the first circumferential direction 101 is clockwise when looking along the longitudinal axis 100 towards the first side 10a of the cap 10. However, in some examples the first circumferential direction may be anticlockwise when looking towards the first side 10a of the cap 10.

As shown in FIG. 1, the barrier 110 includes a first barrier portion 111, a second barrier portion 112 circumferentially spaced from the first barrier portion 111 in the first circumferential direction 101, and a third barrier portion 113 circumferentially spaced from the second barrier portion 112 in the first circumferential direction 101. For completeness, the first barrier portion 111 is circumferentially spaced from the third barrier portion 113 in the first circumferential direction 101. The first barrier portion 111 has a first sidewall 111a and a second sidewall 111b, the second barrier portion 112 has a first sidewall 112a and a second sidewall 112b, and the third barrier portion 113 has a first sidewall 113a and a second sidewall 113b.

The circumferential spacing between the second sidewall 111b of the first barrier portion 111 and the first sidewall 112a of the second barrier portion 112 defines a first slot 121 of the keyway 120 configured to receive a first lug 25a of the lugs 25 of the female luer lock fitting 20. The first lug 25a of the female luer lock fitting is the lug that will first contact the barrier 110 of the cap 10 as the female luer lock fitting 20 is moved axially towards the second side 10b of the cap 10. The circumferential spacing between the second sidewall 112b of the second barrier portion 112 and the first sidewall 113a of the third barrier portion 113 defines a second slot 122 of the keyway 120 configured to receive a second lug 25b (not shown) of the lugs 25 of the female luer lock fitting 20. The circumferential spacing between the second sidewall 113b of the third barrier portion 113 and the first sidewall 111a of the first barrier portion 111 defines a third slot 123 of the keyway 120 configured to receive a third lug 25c of the lugs 25 of the female luer lock fitting 20. The circumferential extent of each of the slots 121, 122, 123 corresponds to the circumferential extent of each of the lugs 25a, 25b, 25c respectively.

In some embodiments, the slots may have the same circumferential extent. In some embodiments, each slot may have a different circumferential extent. In some embodiments, there may be more or less than three slots and the slots may be sized, shaped and/or circumferentially distributed differently to correspond with a female luer lock fitting.

Each of the first sidewalls 111a, 112a, 113a is configured to prevent rotation of the female luer lock fitting 20 in the first circumferential direction 101 when the corresponding lug 25a, 25b, 25c of the female luer lock fitting 20 is circumferentially aligned therewith. Each of the second sidewalls 111b, 112b, 113b is configured to prevent rotation of the female luer lock fitting 20 in the second circumferential direction 102 when the corresponding lug 25a, 25b, 25c of the female luer lock fitting 20 is circumferentially aligned therewith.

In use, when any of the lugs 25a, 25b, 25c of the female luer lock fitting 20 are positioned in the corresponding slots 121, 122, 123, the female luer lock fitting 20 is substantially prevented from rotating relative to the cap 10. The lugs 25 must move axially through the keyway 120 from the first side 10a of the cap 10 to be able to engage the thread 35 of the male luer lock fitting 32.

The cap 10 includes a stopper 130 extending axially from the second barrier portion 112 towards the first side 10a of the cap 10. The stopper 130 includes a stopper wall 131 coplanar with the first sidewall 112a of the second barrier portion 112. That is, the stopper wall 131 is effectively an axial extension of the first sidewall 112a of the second barrier portion 112. The stopper wall 131 is configured to prevent rotation of the female luer lock fitting 20 in the first circumferential direction 101 when the first lug 25a of the female luer lock fitting is circumferentially aligned with the stopper wall 131.

The stopper 130 is positioned so that, in use, a female luer lock fitting 20 may be pushed axially against the barrier 110 and then rotated in the first circumferential direction 101 until the first lug 25a abuts the stopper 130, at which point the female luer lock fitting 20 is aligned to move axially through the keyway 120 of the cap 10 to engage the male luer lock fitting 32 of the fluid line connector 30. Consequently, the stopper 130 advantageously reduces the risk that a user may perpetually rotate the female luer lock fitting 20 in the first circumferential direction 101 in an attempt to correctly align the female luer lock fitting 20 with the keyway 120. As such, the time taken for the user to correctly align the female luer lock fitting 20 with the keyway 120 of the cap 10 may be advantageously reduced.

If the user attempts to over-rotate the female luer lock fitting 20 beyond the correct alignment with the keyway 120, the stopper 130 provides the user with a tactile indication as the first lug 25a abuts the stopper wall 131. Consequently, the stopper 130 may significantly improve the ease of aligning the female luer lock fitting 20 with the keyway 120 of the cap 10 for a user working in substandard conditions (e.g. low light or complete darkness) or for a user having a visual impairment.

As shown in FIG. 1, the stopper 130 includes a sloped surface 135 sloped towards the second barrier portion 112 in the first circumferential direction 101. The sloped surface 135 is configured to guide the first lug 25a over the stopper 130 when the female luer lock fitting 20 is rotated in the second circumferential direction 102. During use, as a user moves the first lug 25a along the sloped surface 135 towards the stopper wall 131, the female luer lock fitting 20 will move axially away from the barrier 10. Once the first lug 25a has moved circumferentially beyond the stopper 130 in the second circumferential direction 102, the female luer lock fitting 20 will move axially toward the barrier 10 under the force provided by the user. Thus, a tactile indication is provided to the user as the first lug 25a moves circumferentially beyond the stopper 130 in the second circumferential direction 102. As the user receives this tactile indication, the female luer lock fitting 20 should be correctly aligned with the keyway 120 or the user may rotate the female luer lock fitting 20 in the first circumferential direction 101 to correctly align the female luer lock fitting 20 with the keyway 120.

Consequently, the user may be provided with a tactile indication of correct alignment between the female luer lock fitting 20 and the keyway 120 regardless of whether the female luer lock fitting 20 is rotated in the first circumferential direction 101 or the second circumferential direction 102. Bi-directional tactile indication may advantageously improve the ease of aligning the female luer lock fitting 20 with the keyway 120 of the cap 10, especially when used in substandard conditions or when the user has a visual impairment.

In certain embodiments, the stopper 130 may extend axially from any of the first barrier portion 111, the second barrier portion 112 and the third barrier portion 113.

As shown in FIG. 1, the first barrier portion 111 includes a top surface 115 facing towards the first side 10a of the cap 10. The top surface 115 has a flat portion 115a normal to the longitudinal axis 100. The second barrier portion 112 has a top surface 116 having a flat portion 116a coplanar with the flat portion 115a of the first barrier portion 111, and the third barrier portion 113 has a top surface 117 having a flat portion 117a coplanar with the flat portion 115a of the first barrier portion 111. As such, the first lug 25a may at least partially rotate between the barrier portions 111, 112, 113 without moving axially relative thereto.

The top surface 115 of the first barrier portion 111 has a sloped portion 115b sloped from the flat portion 115a towards the second side 10b of the cap 10 in the first circumferential direction 101. The sloped portion 115b is adjacent to the second sidewall 111b. As such, the sloped portion 115b is configured to guide the first lug 25a axially toward the first slot 121 as the first lug 25a moves along the sloped portion 115b in the first circumferential direction 101. Consequently, as the user rotates the female luer lock fitting 20 in the first circumferential direction 101, the first lug 25a may move axially towards the first slot 121 without conscious action by the user. Such axial motion may provide the user with a tactile indication that the female luer lock fitting 20 is correctly aligning with the keyway 120.

The sloped portion 115b of the top surface 115 of the first barrier portion 111 may therefore advantageously reduce the time taken to insert the female luer lock portion 20 into the keyway 120, and improve the ease of insertion in substandard conditions or for a user with visual impairment.

In some embodiments, a top surface having a sloped portion may be located on any of the first barrier portion 111, the second barrier portion 112, and the third barrier portion 113.

In some embodiments, the top surface 115 may only have the sloped portion 115b. In some embodiments, the top surface 115 may only have the flat portion 115a.

As shown in FIG. 1, the cap 10 includes a guide portion 140 radially outward of the barrier 110. The guide portion 140 includes a sloped surface 145 sloped radially outwardly towards the first side 10a of the cap 10. The sloped surface 145 continues along the circumference of the barrier 110. The guide portion 140 is configured to guide the female luer lock fitting 20 towards axial alignment with the keyway 120 of the cap 10 when the female luer lock fitting 20 is moved towards the fluid line connector 30. Consequently, a user with visual impairment or a user working under substandard lighting conditions may be able to axially align the female luer lock fitting 20 and the keyway 120 without the need for visual contact. As such, the time taken for the user to axially align the female luer lock fitting 20 with the keyway 120 may be advantageously reduced.

In some embodiments, the sloped surface of the guide portion may extend partially along the circumference of the barrier 110.

The cap 10 may advantageously remove the need for visual contact as the user connects the non-standard female luer lock fitting 20 to the fluid line connector 30 via the keyway 120 of the cap 10. As such, the user may more simply make the connection in substandard conditions (e.g. low or zero light) when compared to using prior art non-standard fluid line connectors. By reducing the difficulty in making the connection, the cap 10 may advantageously reduce the time taken for a user to make the connection when compared to using prior art non-standard fluid line connectors. Simplicity of connection and time taken to connect are both vital characteristics of non-standard fluid line connectors as the user is likely working under pressure and/or multitasking (e.g. attempting to connect multiple fluid lines in a short time period).

As shown in FIG. 2, the cap 10 includes a tactile indicator 150 to aid the user in distinguishing the cap 10 from caps having different keyway configurations. In some embodiments, the female luer lock fitting 20 may include a tactile indicator to aid the user in distinguishing the female luer lock fitting 20 from other non-standard female luer lock fittings having different lug configurations. Indeed, the tactile indicator 150 may advantageously distinguish one cap from another without requiring visual contact.

In some embodiments, the cap may be coupled to the fluid line connector via a living hinge. In other embodiments, the cap may be coupled to the fluid line connector by any suitable means so to prevent a non-corresponding female luer lock fitting from engaging the fluid line connector 30. For example, the cap may screw onto, form a magnetic connection with, or form a friction fit with the fluid line connector. In some embodiments, the cap may be rotatably fixed relative to the fluid line connector.

In certain embodiments, the cap is an injection-moulded plastics material. In some embodiments, the cap and the fluid line connector may be formed monolithically.

In certain embodiments, a cap according to the present invention may be configured to receive a standard female luer lock fitting.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A cap for a fluid line connector having a male luer lock fitting, the cap having a first side and a second side opposite the first side, the cap comprising:
    a barrier defining a keyway, wherein the keyway is centered on a longitudinal axis, the barrier comprising two or more circumferentially-spaced barrier portions, including a first barrier portion and a second barrier portion, to define the keyway, the keyway having at least one slot positioned between the circumferentially-spaced barrier portions that is configured to receive a correspondingly-shaped lug of a correspondingly-shaped female luer lock fitting to permit the correspondingly-shaped female luer lock fitting to pass therethrough, each barrier portion having a first sidewall configured to prevent rotation of the correspondingly-shaped female luer lock fitting in a first circumferential direction when a lug of the correspondingly-shaped female luer lock fitting is circumferentially aligned with the first sidewall; and
    a stopper extending axially from the second barrier portion towards the first side of the cap, wherein the stopper has a stopper wall that is coplanar with the first sidewall of the second barrier portion;
    wherein the shape of the keyway is configured to permit the correspondingly-shaped female luer lock fitting to pass axially therethrough from the first side to engage the male luer lock fitting of the fluid line connector; and wherein the stopper is configured to prevent rotation of the correspondingly-shaped female luer lock fitting in the first circumferential direction when a lug of the correspondingly-shaped female luer lock fitting is circumferentially aligned with the stopper.

2. The cap according to claim 1, wherein each barrier portion has a second sidewall configured to prevent rotation of the correspondingly-shaped female luer lock fitting in a direction opposite the first circumferential direction when a lug of the correspondingly-shaped female luer lock fitting is circumferentially aligned with the second sidewall.

3. The cap according to claim 1, wherein the first barrier portion comprises a top surface facing towards the first side of the cap, the top surface having a sloped portion sloped towards the second side of the cap in the first circumferential direction.

4. The cap according to claim 3, wherein the sloped portion is configured to guide the lug of the correspondingly-shaped female luer lock fitting when the correspondingly-shaped female luer lock fitting is rotated in a direction opposite the first circumferential direction.

5. The cap according to claim 3, wherein the sloped portion of the top surface is adjacent to a second sidewall of the first barrier portion.

6. The cap according to claim 3, wherein the top surface has a flat portion normal to the longitudinal axis.

7. The cap according to claim 6, wherein the flat portion is adjacent to the first sidewall of the first barrier portion.

8. The cap according to claim 1, wherein:
the first barrier portion comprises a top surface facing towards the first side of the cap, the top surface having a sloped portion sloped towards the second side of the cap in the first circumferential direction; and
the second barrier portion is spaced from the first barrier portion in the first circumferential direction to define a slot, of the at least one slots, therebetween so that the stopper is circumferentially opposite to the sloped portion of the first barrier portion.

9. The cap according to claim 1, wherein the stopper has a sloped surface sloped towards the barrier in the first circumferential direction.

10. The cap according to claim 9, wherein the sloped surface of the stopper is configured to guide the lug of the correspondingly-shaped female luer lock fitting when the female luer lock fitting is rotated in a direction opposite to the first circumferential direction.

11. The cap according to claim 1, comprising a guide portion that is radially outward of the barrier, the guide portion having a sloped surface sloped radially outwardly towards the first side of the cap.

12. The cap according to claim 11, wherein the sloped surface of the guide portion extends around a circumference of the barrier.

13. The cap according to claim 1, comprising a part identifier configured to aid a user in distinguishing one keyway shape from another.

14. The cap according to claim 13, wherein the part identifier comprises a tactile indicator.

15. The cap according to claim 1, wherein the cap is a monolithic component.

16. The cap according to claim 1, wherein the cap is configured to couple to a fluid line connector having a male luer lock fitting so that, when coupled, the correspondingly-shaped female luer lock fitting may pass through the cap and threadably connect with the male luer lock fitting.

17. A fluid line connector, comprising:
a male luer lock fitting; and
the cap according to claim 1,
wherein the fluid line connector is configured so that a correspondingly-shaped female luer lock fitting may pass through the cap and threadably connect with the male luer lock fitting.

18. The fluid line connector according to claim 17, wherein the male luer lock fitting and the cap are formed monolithically.

19. An assembly, comprising:
the fluid line connector according to claim 17; and
a female luer lock fitting connectable to the fluid line connector, the female luer lock fitting comprising one or more lugs configured to be received by a thread of the male luer lock fitting of the fluid line connector,
wherein the female luer lock fitting has a radial shape corresponding to the keyway of the cap of the fluid line connector so that the female luer lock fitting may connect with the fluid line connector such that a fluid may flow between the female luer lock fitting and the male luer lock fitting of the fluid line connector.

20. The assembly according to claim 19, wherein the female luer lock fitting comprises a part identifier configured to aid a user in connecting the female luer lock fitting to a correspondingly-shaped keyway of the cap.

21. The assembly according to claim 20, wherein the part identifier comprises a tactile indicator.

22. The cap according to claim 1, wherein the second barrier portion extends a first length in the first circumferential direction; and
wherein the stopper extends a second length in the first circumferential direction that is less than the first length.

23. A cap for a fluid line connector having a male luer lock fitting, the cap having a first side and a second side opposite the first side, the cap comprising:
a barrier defining a keyway, wherein the keyway is centered on a longitudinal axis; and
a stopper extending axially from the barrier towards the first side of the cap;
wherein the shape of the keyway is configured to permit a correspondingly-shaped female luer lock fitting to pass axially therethrough to engage the male luer lock fitting of the fluid line connector;
wherein the stopper is configured to prevent rotation of the correspondingly-shaped female luer lock fitting in a first circumferential direction when a lug of the correspondingly-shaped female luer lock fitting is circumferentially aligned with the stopper; and
wherein the stopper has a sloped surface sloped towards the barrier in the first circumferential direction.

24. The cap according to claim 23, wherein the sloped surface of the stopper is configured to guide the lug of the correspondingly-shaped female luer lock fitting when the female luer lock fitting is rotated in a direction opposite to the first circumferential direction.

25. A cap for a fluid line connector having a male luer lock fitting, the cap having a first side and a second side opposite the first side, the cap comprising:
a barrier defining a keyway, wherein the keyway is centered on a longitudinal axis;
a guide portion that is radially outward of the barrier, the guide portion having a sloped surface sloped radially outwardly towards the first side of the cap; and
a stopper extending axially from the barrier towards the first side of the cap;
wherein the shape of the keyway is configured to permit a correspondingly-shaped female luer lock fitting to pass axially therethrough to engage the male luer lock fitting of the fluid line connector; and wherein the stopper is configured to prevent rotation of the correspondingly-shaped female luer lock fitting in a first circumferential direction when a lug of the correspondingly-shaped female luer lock fitting is circumferentially aligned with the stopper.

26. The cap according to claim 25, wherein the sloped surface of the guide portion extends around a circumference of the barrier.

* * * * *